United States Patent
Shoa'a

(10) Patent No.: US 6,777,448 B2
(45) Date of Patent: Aug. 17, 2004

(54) VETERINARY COMPOSITIONS FOR THE TREATMENT OF PARASITIC DISEASES

(75) Inventor: Abdul Rahman Shoa'a, Lund (SE)

(73) Assignee: New Pharma Research Sweden AB, Lund (SE)

( * ) Notice: Subject to any disclaimer, the term of this patent is extended or adjusted under 35 U.S.C. 154(b) by 395 days.

(21) Appl. No.: 10/220,393

(22) PCT Filed: Feb. 22, 2001

(86) PCT No.: PCT/EP01/02037

§ 371 (c)(1),
(2), (4) Date: Aug. 29, 2002

(87) PCT Pub. No.: WO01/64222

PCT Pub. Date: Sep. 7, 2001

(65) Prior Publication Data

US 2003/0049309 A1 Mar. 13, 2003

(30) Foreign Application Priority Data

Feb. 29, 2000 (EP) .......................................... 00104126

(51) Int. Cl.$^7$ ..................... A61K 47/32; A61K 31/165; A61K 31/40
(52) U.S. Cl. .................... 514/772.5; 514/617; 514/622; 514/423
(58) Field of Search .............................. 514/772.5, 617, 514/622, 423

(56) References Cited

U.S. PATENT DOCUMENTS 4,128,632 A * 12/1978 Lo et al. .................. 424/78.24

FOREIGN PATENT DOCUMENTS

| AU | 53511/79 | * | 2/1983 |
| EP | 0 136 033 | | 4/1985 |
| EP | 01 137 627 | | 4/1985 |
| EP | 0 202 568 | | 11/1986 |
| FR | 2 275 217 | | 1/1976 |
| GB | 1 472 385 | | 5/1977 |
| WO | WO 95/16447 | | 6/1995 |
| WO | 95/16447 | * | 6/1995 |

OTHER PUBLICATIONS

Database WPI, Section Ch, Week 198609, Derwent Publications Ltd., London, GB, Class B02, A 1986–061936, XP002167524 & ZA 8 402 571 A (Merck & Co Inc), Oct. 7, 1985, abstract.
International Search Report of PCT/EP 01/02037.

* cited by examiner

*Primary Examiner*—Thurman K. Page
*Assistant Examiner*—Blessing Fubara
(74) *Attorney, Agent, or Firm*—Peter F. Corless; Dianne M. Rees; Edwards & Angell, LLP

(57) ABSTRACT

Micellar non-aqueous or aqueous compositions for the therapeutic treatment of animal diseases caused by parasitic worms or nematodes, comprising rafoxanide and specific combinations of solvents which act as stabilising and absorption promoting agents. The solvents are selected from non-ionic surface-active agents such as Tween®-80 and from N-methylpyrrolidone, 2-pyrrolidone or dimethylsulfoxide. The compositions are easy to prepare, stable upon storage and can be administered orally, by injection or topically. With these formulations, an improvement of the efficacy of rafoxanide in the treatment of the diseases is observed.

18 Claims, No Drawings

VETERINARY COMPOSITIONS FOR THE TREATMENT OF PARASITIC DISEASES

This application is a 371 of PCT/EP01/02 037 filed Feb. 22, 2001.

FIELD OF THE INVENTION

The present invention concerns compositions comprising rafoxanide, the compositions being intended to be used in the veterinary field, and preferably for the treatment of parasitic diseases in farm and domestic animals, like the liver fluke or bot fly infestations.

BACKGROUND OF THE INVENTION

Rafoxanide is the generic name of 3'-chloro-4'-(4-chlorophenoxy)-3,5-di-iodosalicylanilide. Rafoxanide is sold, for example, by the company Pfizer Animal Health Inc., Zimbabwe, under the trade name Ranox®, or by the company Ventron, India.

It is known that rafoxanide is useful as an anthelmintic and fasciolicide agent and is active for the treatment of parasitic diseases affecting animals and caused by parasitic worms or nematodes infestations.

It is also known that rafoxanide is extremely water insoluble (see for example Nessel, GB patent 1 472 385), its solubility in water at 25° C. being approximately 0.005% weight/volume.

Attempts to improve the solubilisation of rafoxanide by adding surface-active agents in the composition have been made. The results have shown that in a 1% surface-active agent composition, the solubility of rafoxanide is 0.14%.

This has the drawback that, when given orally, the absorption of rafoxanide by the body is low. As a consequence, its plasma concentration in the body is also low, and the majority of the active substance is unabsorbed and excreted in the faeces. For example, the absorption may be as low as 10% in non-gastric species, and only up to 50% or less in ruminants where the rumen aids in the absorption process.

As far as the anthelmintic activity is directly related to the plasma concentration of rafoxanide, to achieve a sufficient plasma concentration, a high dose of rafoxanide must be given to the subject to be treated, which is clearly economically disadvantageous.

Another solution would be to deliver the drug via injection, but here again, rafoxanide has been shown to be irritating and it is therefore not desirable to inject it as such.

In addition, rafoxanide is known to persist in the bloodstream of animals and to bind strongly to protein in the blood. This can lead to toxicity, which is clearly undesirable in the case of animals which are slaughtered for human consumption.

Several studies have been conducted to improve the absorption of rafoxanide by the body or its solubility in a composition which would be acceptable for administration.

Nessel (GB Patent 1 472 385) describes an aqueous composition which contains rafoxanide, polyvinylpyrrolidone and a caustic agent like sodium hydroxide or the sodium salt of cholic acid, deoxycholic acid, stearic acid or isostearic acid. According to the author, the presence of polyvinylpyrrolidone and of the caustic agent in the composition enhances the solubility of the active agent to such an extent that an aqueous composition containing up to 7.5% of rafoxanide can be prepared.

However, polyvinylpyrrolidone is an expensive material and, as mentioned in Nessel, the molecular weight of the polyvinylpyrrolidone molecules varies widely within the range of about 10,000 to about 360,000. This causes a drawback in the use of polyvinylpyrrolidone since only biologically pure grades of polyvinylpyrrolidone exempts of pyrogens and other toxic materials and with a molecular weight of 3,000 to 50,000 should be used.

In a similar manner, Lo et al. (U.S. Pat. No. 4,128,632) describes an aqueous composition which contains a complex of rafoxanide and polyvinylpyrrolidone. The process for the preparation of the composition differs from the process of Nessel by the use of a specific solvent like acetone or glycerol formal, which can optionally be removed by evaporation. According to Lo et al., the advantage over Nessel is that the process is faster and less expensive since it does not require the expensive step of spray drying of the rafoxanide/polyvinylpyrrolidone complex formed in the solvent before its dissolution in water.

However, in addition to the drawbacks mentioned above for the compositions of Nessel and which are due to the use of polyvinylpyrrolidone, the compositions of Lo et al. may also contain traces of acetone, which is a toxic chemical compound not desired in veterinary or pharmaceutical compositions.

It should also be noted that the processes of Nessel or Lo et al. both contain a step of heating the composition at a temperature higher than +40° C. which, at an industrial level, is an expensive and inconvenient step.

In another reference, Burke (WO 95/16447) describes an anthelmintic composition for oral administration containing 4.5% rafoxanide and 3% of another insoluble nematocidal agent belonging to the benzimidazole derivatives, fenbendazole. The compositions are micronised compositions, i.e. in the form of a suspension of particles, and contain also several additional components such as xanthan gum, polyvinylpyrrolidone and a dispersing agent. The author reports that the composition shows an improved anthelmintic effect without undesirable toxic side effects. The improved effect is connected with an increased plasma concentration of fenbendazole, originated by the combined administration of both agents. However, no improvement of the absorption of rafoxanide is reported.

From the above examples, it can be concluded that there is still a need for a composition for the treatment of parasitic diseases in animals which is based on the active substance rafoxanide, which can be prepared in an easy way, which is sufficiently concentrated to permit satisfactory dosage forms and which, when administered parenterally, topically or orally, shows good absorption characteristics by the body.

Surprisingly, the inventor of the present invention has found that the efficacy of rafoxanide in the treatment of parasitic diseases in animals is improved when it is dissolved in a specific combination of solvents which is able to keep the active molecule in a micellar stable state in the composition even at high concentrations. Thus, the resulting composition is a non-aqueous micellar composition.

A stable composition in the meaning of the present invention is a composition wherein the compounds are present in a soluble form, i.e. there is for example no precipitate, the composition also remaining stable during storage.

The inventor of the present invention has also found that, if necessary, water can be added to the composition, to obtain an aqueous micellar composition.

The inventor of the present invention has also found that said compositions are particularly effective in the treatment of parasitic worms or nematodes infestations in animals, like for example the liver fluke in cattle, buffaloes, sheep and goats, the blood sucking nematodes infestations, and the larval stages of the nasal bot fly infestation in sheep and goats.

Thus, the main object of the present invention is to provide new anthelmintic and fasciolicide compositions.

Another object of the present invention is to provide these compositions as compositions which are stable upon storage.

Another object of the present invention is to provide these compositions as compositions which can be administered orally, topically or parenterally (e.g. by injection).

One of the advantages of the present invention is therefore that the composition can be prepared in an easy manner, i.e. by simply mixing the components together, and without the addition of expensive or toxic substances.

Another advantage of the present invention is that the compositions have good absorption characteristics when compared to the above mentioned known compositions of the prior art.

Further problems which can be solved by this invention with respect to known prior art compositions will become apparent to the reader of the following description.

SUMMARY OF THE INVENTION

The present invention provides a solution to the aforementioned problems.

The aforementioned object is achieved by a micellar composition having the features defined in claim 1 and comprising as an essential active ingredient rafoxanide and a combination of solvents which act as a stabilizing and absorption-promoting agent, the combination being selected from a group consisting of specific combinations of a non-ionic surface active agent such as Tween® 80 with N-methylpyrrolidone (NMP), 2-pyrrolidone, dimethylsulfoxide (DMSO), or specific combinations thereof.

The aforementioned object is also achieved by the use of the micellar composition for the treatment of diseases, and most preferably diseases due to parasitic worms or nematodes infestations in animals like sheep, goats, buffalos or cattle.

Preferred embodiments of the invention, including the use of preferred concentrations, the addition of optional ingredients in the composition like for example glycerol formal, water, excipients, preservatives, vitamins, further stabilizing agents, carriers, antioxidants, photostabilizers, colorants, further absorption-promoting substances, or the use of the composition for the treatment of specific diseases in animal are defined in the dependent claims.

A combination of anthelmintic antibiotics selected from the group consisting of avermectins or their derivatives, such as avermectin and ivermectin, with the micellar composition comprising rafoxanide as defined in claim 1, and the use of this combination for the treatment of specific diseases in animal, are also defined in the dependent claims.

Unless otherwise specified, the percentages of ingredients used in the compositions are defined as weight per volume. The preferred concentrations or ranges of concentrations mentioned hereafter are concentrations which are more suitable to achieve the object of the present invention.

DESCRIPTION OF PREFERRED EMBODIMENTS

The micellar composition according to the present invention comprises as an essential active ingredient rafoxanide and a combination of solvents which act as a stabilising and absorption-promoting agent.

The amount of rafoxanide in the composition is preferably between 2.5 and 25% weight/volume. Most preferably, the composition contains 12.5% weight/volume of rafoxanide.

The combination of solvents which act as a stabilising and absorption-promoting agent always comprise a non-ionic surface active agent such as Tween® 80 (commercial name of polyoxyethylene sorbitan monooleate) or Cremophor® (commercial name of polyoxyethylated castor oil), which is necessary for the formation of the micelles, and at least a further solvent selected from N-methylpyrrolidone (NMP), 2-pyrrolidone and dimethylsulfoxide (DMSO).

Preferably, the combination of solvents is a combination of Tween® 80 with NMP, or Tween® 80 with 2-pyrrolidone, or Tween® 80 with NMP and 2-pyrrolidone, or Tween® 80 with DMSO and NMP and/or 2-pyrrolidone. These combinations may contain additionally glycerol formal, which acts as filler or cosolvent.

It should be noted that when DMSO and/or glycerol formal are the only solvents added in a composition containing rafoxanide and Tween® 80, a precipitate will form when the composition is kept at a low temperature. Therefore, it is recommended to always combine DMSO and/or glycerol formal with either NMP or 2-pyrrolidone.

The amount of Tween® 80 in the composition is preferably between 5% and 50% weight/volume.

The compositions may also comprise optionally other agents like excipients, preservatives, vitamins, further stabilising agents, carriers, antioxidants, photostabilisers, colorants, further absorption-promoting substances, thickeners or any other agent or additive commonly used in veterinary or medical compositions which is for example useful for the stability of the composition or permits to improve the formulation for a specific way of administration without altering the anthelmintic or fasciolicide activity.

When necessary, the composition may be diluted with water, in order to obtain an aqueous micellar composition. Acetic acid should then be added in the composition to improve the stability and solubility of the components in the composition.

The composition may also comprise in addition an anthelmintic antibiotic selected from the group consisting of avermectins or their derivatives, such as for example avermectin or ivermectin.

Avermectins were isolated as compounds possessing anthelmintic activity from the culture broth of an actinomycete strain. Chemically, avermectins are oleandrose disaccharide derivatives of 16-membered pentacyclic lactones. The avermectin complex is a family of four closely related major components, A1a, A2a, B1a and B2a, and four minor components, A1b, A2b, B1b and B2b, which are lower homologues of the major components. Ivermectin, an hydrogenated product of the B1 component (22,23-dihydroavermectin B1), is used as an important anthelmintic in veterinary fields and for the control of onchocerciasis in human.

When combining avermectin or ivermectin with rafoxanide in a composition in accordance with the present invention, the composition is especially indicated for the treatment of diseases caused by internal and external parasites affecting cattle, buffaloes, sheep and goats. Examples of internal parasites aimed at are adult and immature round worms, young (6 to 10 weeks old) and adult liver flukes, and tissue invading fly maggots such as larvae of cattle warble fly and sheep nostril fly. Examples of external parasites aimed at are parasites causing mange, ticks and lice.

The amount of avermectin or ivermectin in the composition is preferably between 0% and 15% weight/volume.

The preferred combination is a combination of rafoxanide with ivermectin. The best ratio between rafoxanide and ivermectin in the composition, or in other words the ratio that provides the best effect, can be easily determined via a routine experiment. In one embodiment, the composition preferably comprises 12% of rafoxanide and 0.8% of ivermectin.

Generally, the compositions are intended to be administered orally, topically or by injection and will be prepared in a suitable form. However, it should be noted that the form in which the compositions are administered depends upon the particular infection to be treated and may be adapted in order, for example, to deliver the agent closer to the site of infection. Thus, in the case of infections of a topical nature, a formulation for topical application may be prepared and topical application may be used.

The compositions are effective for the treatment of diseases in animals, in particular the treatment of infestations by parasitic worms or nematodes in animals.

The parasitic worms or nematodes include, for example, worms or nematodes of the following types: *Fasciola hepatica, Fasciola gigantica, Haemonchus placei, Bunostomum phlebotomum* and *Oesophagostomum radium*.

In the case of a combination with avermectin or ivermectin, the compositions are, as already mentioned above, more specifically effective for the treatment of diseases caused by internal and external parasites affecting cattle, buffaloes, sheep and goats.

The posology and way of administration depend on the subject to be treated and the stage and severity of the infestation.

For example, for systemic treatment of cattle infested by liver fluke, the composition is administered by subcutaneous injection and rafoxanide is given at a single dose of 3 mg/kg body weight.

In the case of a composition comprising a combination of 12% rafoxanide with 0.8% ivermectin, the composition may, for example, also be administered by subcutaneous injection such that rafoxanide is given at a dose of 3 mg/kg body weight, and ivermectin is then given at a dose of 0.2 mg/kg body weight.

The invention will now be described in more detail with reference to the following examples.

EXAMPLES

The amounts of ingredients are given in % of weight/volume. The volume is adjusted by addition of deionized water. The abbreviation q.s.p. means "quantity sufficient per".

Example 1:
A composition comprising:

| | |
|---|---|
| Rafoxanide | 2.5% |
| NMP | 4% |
| Tween ® 80 | 10% |
| 2-pyrrolidone | q.s.p. 100 ml |

Example 2:
A composition comprising:

| | |
|---|---|
| Rafoxanide | 2.5% |
| Tween ® 80 | 8% |
| NMP | q.s.p. 100 ml |

Example 3:
A composition comprising:

| | |
|---|---|
| Rafoxanide | 2.5% |
| 2-pyrrolidone | 30% |
| Tween ® 80 | 10% |
| DMSO | 20% |
| NMP | q.s.p. 100 ml |

Example 4:
A composition comprising:

| | |
|---|---|
| Rafoxanide | 2.5% |
| 2-pyrrolidone | 20% |
| Tween ® 80 | 8% |
| NMP | 20% |
| Glycerol formal | q.s.p. 100 ml |

Example 5:
A composition comprising:

| | |
|---|---|
| Rafoxanide | 12.5% |
| NMP | 28% |
| Tween ® 80 | 20% |
| Glycerol formal | q.s.p. 100 ml |

Example 6:
A composition comprising:

| | |
|---|---|
| Rafoxanide | 15% |
| Tween ® 80 | 40% |
| NMP | q.s.p. 100 ml |

Example 7:
A composition comprising:

| | |
|---|---|
| Rafoxanide | 6.25% |
| Glycerol formal | 40% |
| Tween ® 80 | 20% |
| NMP | q.s.p. 100 ml |

Example 8:
A composition comprising:

| | |
|---|---|
| Rafoxanide | 12.5% |
| 2-pyrrolidone | 40% |
| Tween ® 80 | 10% |
| Glycerol formal | q.s.p. 100 ml |

Example 9:
A composition comprising:

| | |
|---|---|
| Rafoxanide | 2.5% |
| Acetic acid | 10% |
| Tween ® 80 | 10% |
| NMP | 60% |
| Water | q.s.p. 100 ml |

Example 10:
A composition comprising:

| | |
|---|---|
| Rafoxanide | 12% |
| Ivermectin | 0.8% |
| Tween ® 80 | 40% |
| NMP | q.s.p. 100 ml |

The ingredients are mixed at room temperature and give a clear solution, which can be used for injections and is miscible with water in all proportions.

All the above exemplified compositions are stable upon storage at least for two years at room temperature (+25° C. +/−2° C.)

The following examples illustrate the efficacy of the compositions of the present invention and their industrial applicability.

Evaluation of the Efficacy of a Composition in Accordance with the Present Invention in the Treatment of Liver Fluke Infestation in Cattle The aim of this study was to evaluate the effect of a treatment with a composition in accordance with the present invention (composition of Example 5) on liver fluke infestation in cattle, and to compare the efficacy of this treatment with the efficacy of a treatment with a 2.5% aqueous rafoxanide suspension.

Thus, the following experiment was carried out.

A group of calves infested experimentally or naturally with one or more liver flukes of the *Fasciola hepatica* or *Fasciola gigantica* type or with gastrointestinal parasites of the *Haemonchus placei, Bunostomum phlebotomum* or *Oesophagostomum radium* type, each of immature or adult type, was used in the experiment.

Prior to the initiation of the tests, all animals were confirmed to be positively infested by identification of eggs of the parasites in the faeces.

The animals were then separated into four groups, and treated as follows. Three groups were treated by a single subcutaneous injection of a composition in accordance with Example 5 of the present invention, and respectively at a dose of rafoxanide of 1, 2 or 3 mg/kg body weight. The last group was treated with a single dose of rafoxanide suspension at a dose of 7.5 mg/kg of body weight.

Eight days after the treatment, the animals were killed. In the case of the animals infested by *Fasciola hepatica* or *Fasciola gigantica*, the flukes were collected from the liver, gall bladder and bile duct and counted. In the case of the other infestations, the entire gastrointestinal content was examined for a counting of the number of parasites present.

In each case, the results of the tests were compared to the results obtained with infested animals which did not receive any treatment.

The results are summarised in the following Table I where the effect of the treatment is expressed as a percentage of reduction of the number of parasites.

TABLE I

% of reduction of the number of parasites

| Type of treatment | Composition of Ex. 5 | Composition of Ex. 5 | Composition of Ex. 5 | 2.5% rafoxanide suspension |
|---|---|---|---|---|
| Dose in mg/kg body weight | 1 | 2 | 3 | 7.5 |
| Parasites adult type | | | | |
| F. hepatica | 83 | 98 | >99 | 93 |
| F. gigantica | >99 | >99 | >99 | 95 |
| H. Placei | 89 | 93 | >99 | 97 |
| B. phlebotomum | 97 | 99 | >99 | 91 |
| O. radium | 52 | 88 | >99 | 89 |
| Parasites immature type | | | | |
| F. hepatica | 45 | 88 | 89 | 82 |
| F. gigantica | 37 | 74 | 87 | 79 |
| H. Placei | 35 | 92 | 99 | 92 |
| B. phlebotomum | 41 | 90 | 95 | 87 |
| O. radium | 47 | 80 | 88 | 77 |

As is clear from Table I, the treatment with a composition in accordance with Example 5 of the present invention is more effective in reducing the number of parasites associated with the infestation than the treatment using a suspension of rafoxanide in accordance with the prior art, and this even if a lower dose of rafoxanide is given to the animal.

Evaluation of the Efficacy of a Composition in Accordance with the Present Invention in the Treatment of Liver Fluke Infestation in Buffaloes The aim of this study was to evaluate the effect of a treatment with a composition in accordance with the present invention (composition of Example 5) on liver fluke infestation in buffaloes, and to compare the efficacy of this treatment with the efficacy of a treatment with a 2.5% aqueous rafoxanide suspension.

Thus, the following experiment was carried out.

A group of 15 buffaloes infested naturally with *Fasciola gigantica* was used in the experiment.

Prior to the initiation of the tests, all animals were confirmed to be positively infested by identification of eggs of the parasites in the faeces.

The animals were then separated into three groups each of five animals, and treated as follows. The first group was untreated and served as control. The second group was treated by a single subcutaneous injection of a composition in accordance with Example 5 of the present invention, at a dose of rafoxanide of 3 mg/kg body weight. The third group was treated with a single dose of rafoxanide suspension at a dose of 7.5 mg/kg of body weight.

Ten, eighteen and fifty days after the treatment, a counting of the number of parasites present in the faeces was effected.

The results are summarised in the following Table II.

TABLE II

No. of eggs per gram of faeces

| Animal group | Before treatment | 10 days after treatment | 18 days after treatment | 50 days after treatment |
|---|---|---|---|---|
| Control | | | | |
| 1 | 56 | 47 | 44 | 49 |
| 2 | 28 | 30 | 30 | 31 |
| 3 | 42 | 42 | 40 | 41 |
| 4 | 80 | 60 | 58 | 68 |
| 5 | 52 | 62 | 42 | 57 |
| Composition of Example 5 (3 mg/kg body weight) | | | | |
| 6 | 64 | — | — | — |
| 7 | 80 | — | — | — |
| 8 | 32 | — | — | — |
| 9 | 42 | — | — | — |
| 10 | 70 | — | — | — |
| Rafoxanide suspension (7.5 mg/kg body weight) | | | | |
| 11 | 55 | 7 | 6 | 2 |
| 12 | 78 | 6 | 4 | — |
| 13 | 44 | 1 | 4 | 3 |
| 14 | 38 | 3 | 7 | — |
| 15 | 69 | 5 | 1 | 2 |

As is clear from Table II, the treatment with a composition in accordance with Example 5 of the present invention is more effective in reducing the number of parasites associated with the infestation than the treatment using a suspension of rafoxanide in accordance with the prior art, and this even if a lower dose of rafoxanide is given to the animal.

Evaluation of the Efficacy of a Composition in Accordance with the Present Invention in the Treatment of Liver Fluke Infestation in Sheep The aim of this study was to evaluate the effect of a treatment with a composition in accordance with the present invention (composition of Example 5) on liver fluke infestation in sheep, and to compare the efficacy of this treatment with the efficacy of a treatment with a 2.5% aqueous rafoxanide suspension.

Thus, the following experiment was carried out.

A group of sheep was infested with *Fasciola hepatica* by inoculation of 250 viable metacercariae/animal.

Prior to the initiation of the tests, all animals were confirmed to be positively infested by identification of eggs of the parasites in the faeces.

The animals were then separated into four groups, and treated as follows. Three group were treated by a single subcutaneous injection of a composition in accordance with Example 5 of the present invention, and respectively at a dose of rafoxanide of 1, 2 or 3 mg/kg body weight. The last group was treated with a single dose of rafoxanide suspension at a dose of 7.5 mg/kg of body weight.

Seven days after the treatment, the animals were killed. The flukes were collected from the liver, gall-bladder and bile duct and counted.

In each case, the results of the tests were compared to the results obtained with infested animals which did not receive any treatment.

The results are summarised in the following Table III where the efficacy of the treatment is expressed as a percentage of reduction of the number of parasites.

TABLE III

Average number of flukes and efficacy

| Dose | Average number of flukes | Efficacy in % |
|---|---|---|
| Control | | |
| | 134.0 +/− 3.4 | — |
| Composition of Example 5 | | |
| 1 mg/kg body weight | 18.2 +/− 1.3 | 86.4 |
| 2 mg/kg body weight | 7.1 +/− 0.8 | 94.7 |
| 3 mg/kg body weight | 1.2 +/− 0.11 | 99.1 |
| Rafoxanide suspension | | |
| 7.5 mg/kg body weight | 4.7 +/− 0.21 | 96.5 |

As is clear from Table III, the treatment with a composition in accordance with Example 5 of the present invention is more effective in reducing the number of parasites associated with the infestation than the treatment using a suspension of rafoxanide in accordance with the prior art, and this even if a lower dose of rafoxanide is given to the animal.

The compositions according to the present invention can therefore be used as a treatment for animals infested by liver flukes or gastrointestinal parasites.

Although the present invention has been described with reference to several examples and embodiments of specific compositions and concentrations of ingredients, this is not to be considered as a limitation of the invention but merely illustrative thereof.

Specifically, other compounds like chemical derivatives of the active compounds cited herein could be used, as soon as the modification does not lead to a substantial loss of the activity of the compound.

What is claimed is:

1. A micellar composition for the treatment of parasitic diseases in animals, said composition comprising rafoxanide, a non-ionic surface active agent, and either N-methylpyrrolidone, or 2-pyrrolidone, or a combination of N-methylpyrrolidone with 2-pyrrolidone, or the combination of dimethylsulfoxide with N-methylpyrrolidone and/or 2-pyrrolidone.

2. A composition according to claim 1 wherein the non-ionic surface active agent is polyoxyethylene sorbitan monooleate.

3. A composition according to claim 1, which further comprises glycerol formal.

4. A composition according to claim 1 wherein amount of rafoxanide is between 2.5% and 25% weight/volume.

5. A composition according to claim 1 wherein amount of rafoxanide is 12.5% weight/volume.

6. A composition according to claim 1 wherein amount of non-ionic surface-active agent is between 5 and 50% weight/volume.

7. A composition according to claim 1, which further comprises water and acetic acid.

8. A composition according to claim 1 which further comprises one or more agents of excipients, preservatives, vitamins, further stablising agents, carriers, antioxidants, photostabilisers, colorants, further absorption-promoting substances, or thickeners.

9. A composition according to claim 1, which further comprises an anthelmintic antibiotic selected from the group consisting of avermectins or their derivatives.

10. A composition according to claim 9 wherein the amount of avermectin or derivative thereof in the composition is between 0% and 15% weight/volume.

11. A composition according to claim 9 wherein the anthelmintic antibiotic is ivermectin.

12. A composition according to claim 11, which comprises 12% of rafoxanide and 0.8% of ivermectin.

13. A method for treating an animal suffering from or susceptible to a disease caused by parasitic worms or nematodes, comprising administering to the animal an effective amount of a composition of claim 1.

14. The method of claim 13 wherein the animal is cattle, buffalo, sheep or goat.

15. A method for treating an animal suffering from or susceptible to a disease caused by parasitic worms or nematodes, comprising administering to the animal an effective amount of a composition of claim 1.

16. The method of claim 15 wherein the animal is cattle, buffalo, sheep or goat.

17. A method for treating an animal suffering from or susceptible to a disease caused by parasites, comprising administering to the animal an effective amount of a composition of claim 1.

18. The method of claim 15 wherein the animal is cattle, buffalo, sheep or goat.

* * * * *